United States Patent
Yanai et al.

(12)

(10) Patent No.: US 6,566,111 B1
(45) Date of Patent: May 20, 2003

(54) β-FRUCTOFURANOSIDASE AND GENE THEREOF

(75) Inventors: Koji Yanai, Sakado (JP); Akitaka Nakane, Sakado (JP); Toshiaki Kono, Sakado (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 09/508,264

(22) PCT Filed: Sep. 10, 1998

(86) PCT No.: PCT/JP98/04087
§ 371 (c)(1),
(2), (4) Date: Mar. 9, 2000

(87) PCT Pub. No.: WO99/13059
PCT Pub. Date: Mar. 18, 1999

(30) Foreign Application Priority Data

Sep. 10, 1997 (JP) ............................................. 9-245154

(51) Int. Cl.[7] ............................. C12N 9/24; C07K 14/00
(52) U.S. Cl. ....................... 435/200; 435/183; 435/193; 530/350; 536/232
(58) Field of Search ................................. 435/200, 183, 435/193; 530/350; 436/232

(56) References Cited

U.S. PATENT DOCUMENTS 6,337,201 B1 * 11/2002 Yanai et al. ................. 435/200

FOREIGN PATENT DOCUMENTS

WO          97/34004          9/1997

OTHER PUBLICATIONS

Hatakeyama et al. [J. Ferment. Bioeng., 1996, 81(6) : 518–23, Abstract only].*

L. M. Boddy et al., "Purification and Characterization of an Aspergillus nigar invertase and its DNA sequence", Curr. Genet., vol. 24, pp. 60–66, 1993.

* cited by examiner

*Primary Examiner*—Tekchand Saidha
(74) *Attorney, Agent, or Firm*—Wenderoth, Lind & Ponack, L.L.P.

(57) ABSTRACT

A novel β-fructofuranosidase and its gene are disclosed. A polypeptide comprising the amino acid sequence of SEQ ID No. 1 or No. 3 is an enzyme having β-fructofuranosidase activity and high transferase activity, and is capable of efficiently producing fructooligosaccharides.

1 Claim, 6 Drawing Sheets

β-FRUCTOFURANOSIDASE AND GENE THEREOF

BACKGROUND OF THE INVENTION

1. Field of the Invention

The present invention relates to a β-fructofuranosidase having a fructose transferase activity, which is useful for the industrial production of fructooligosaccharides, and its gene and use.

2. Description of the Related Art

The molecular structure of a fructooligosaccharide is the same as that of sucrose, except that the fructose half of a fructooligosaccharide is coupled with another one to three fructose molecules at positions C1 and C2 via a β-bond. Fructooligosaccharides are indigestible sugars known for their physiological advantages, such as the facilitation of Bifidobacterial growth in the intestines, metabolic stimulation for cholesterols and other lipids, and little cariosity.

Fructooligosaccharides are found in plants, such as asparagus, onion, Jerusalem-artichoke and honey. They are also synthesized from sucrose by the newly industrialized mass production technique using fructosyltransfer reaction which is catalyzed by a β-fructofuranosidase derived from a microorganism.

The molecular structure of 1-kestose and nystose, which make up component of industrially produced fructooligosaccharide mixtures of today, are the same as that of sucrose except that their fructose half is coupled with one and two molecules of fructose, respectively. It has been found recently that their high-purity crystals exhibit new desirable characteristics both in physical properties and food processing purpose while maintaining the general physiological advantages of fructooligosaccharides (Japanese Patent Application No. 222923/1995, Japanese Laid-Open Publication No. 31160/1994). In this sense, they are fructooligosaccharide preparations having new features.

In consideration of the above, some of the inventors have already proposed an industrial process for producing crystal 1-ketose from sucrose (Japanese Patent Application No. 64682/1996, Japanese Patent Application No. 77534/1996, and Japanese Patent Application No. 77539/1996). According to this process, a β-fructofuranosidase harboring fructosyltransferase activity is first allowed to act on sucrose to produce 1-kestose; the resultant 1-kestose is fractionated to a purity of 80% or higher by chromatographic separation; then, using this fraction as a crystallizing sample, crystal 1-kestose is obtained at a purity of 95% or higher. The β-fructofuranosidase harboring fructosyltransferase activity used in this process should be able to produce 1-kestose from sucrose at a high yield while minimizing the byproduct nystose, which inhibits the reactions in the above steps of chromatographic separation and crystallization. In the enzyme derived from *Aspergillus niger*, which is currently used for the industrial production of fructooligosaccharides mixtures, the 1-kestose yield from sucrose is approximately 44%, while 7% is turned to nystose (Japanese Patent Application No.64682/1996). These figures suggest that the enzyme has room for improvement in view of the industrial production of crystal 1-ketose.

As a next step, some of the inventors have successfully screened new enzymes having more favorable characteristics from *Penicillium rogueforti* and *Scopulariopsis brevicaulis*. These enzymes were able to turn 47% and 55% of sucrose into 1-kestose, respectively, and 7% and 4% to nystose (Japanese Patent Application No. 77534/1996, and Japanese Patent Application No. 77539/1996). These enzymes are inferior in productivity and stability to the enzyme derived from *Aspergillus niger*, and have room for improvement in view of the industrial production of crystal 1-ketose.

Thus, some of the inventors had paid attention to the procedure of genetic engineering as a process for improving the productivity of the enzyme, isolated the gene encoding β-fructofuranosidase from *Penicillium roqueforti* and *Scopulariopsis brevicaulis*, respectively, and conducted the structure analysis (PCT/JP97/00757). As a result, the translation regions encoding 565 amino acids and 574 amino acids as a mature protein were respectively deduced in the β-fructofuranosidase genes from *Penicillium roqueforti* and *Scopulariopsis brevicaulis* and their expression products were shown to have β-fructofuranosidase activity, like the β-fructofuranosidase gene from *Aspergillus niger* (L.M. Boddy et al., Curr. Genet., 24, 60–66 (1993)).

SUMMARY OF THE INVENTION

The inventors have now found that the addition of 38 and 39amino acids to the C-terminal of the β-fructofuranosidase genes from *Penicillium roqueforti* and *Scopulariopsis brevicaulis*, which were previously found by some of the inventors, improves its activity.

Thus, an object of the present invention is to provide a novel β-fructofuranosidase and its gene.

The novel β-fructofuranosidase according to the present invention is a polypeptide comprising the amino acid sequence of SEQ ID No. 1 or 3 or a homologue thereof.

Furthermore, the gene according to the present invention is a DNA encoding the above polypeptide.

The amino acid sequence of SEQ ID No. 1 or 3 according to the present invention is constructed by adding 38 and 39 amino acids to the C-terminals of the β-fructofuranosidase genes from *Penicillium roqueforti* and *Scopulariopsis brevicaulis*, which were previously found by some of the inventors as described above. It has been found that an intron actually exists at the region of the β-fructofuranosidase gene, which was presumed to encode the C-terminal amino acids by some of the present inventors and that the β-fructofuranosidase genes further encode 38 and 39 amino acids of the C-terminal. Surprisingly, the β-fructofuranosidase activity was remarkably improved by adding these amino acids to the C-terminal, as compared with the protein to which these sequences are not added.

DESCRIPTION OF THE PREFERRED EMBODIMENTS

β-Fructofuranosidase

Figure 1A:
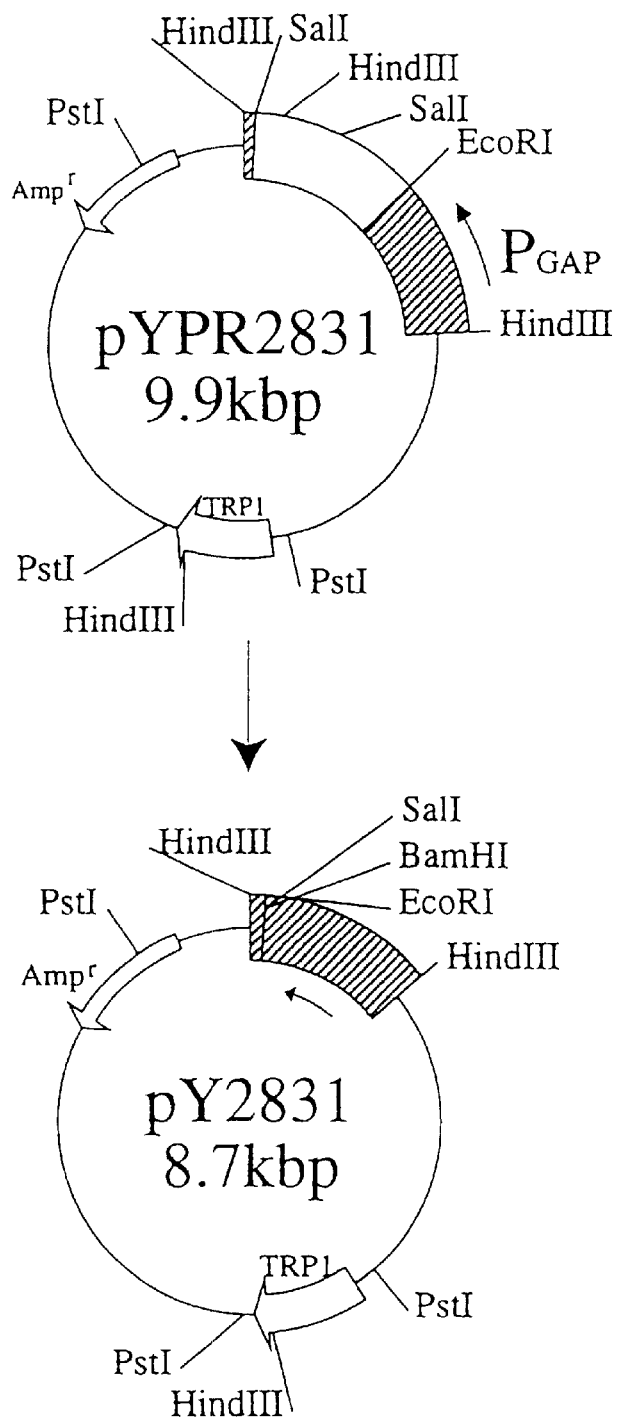
FIGS. 1A, B, C and D show the construction of expression vector pYPEN02 in which a gene encoding the enzyme protein consisting of the amino acid sequence of SEQ ID No. 1 is introduced, and expression vector pYPEN01 in which a gene encoding the enzyme protein consisting of the amino acid sequence from 1 to 565 of amino acid sequence of SEQ ID No. 1 is introduced.
Figure 1B:
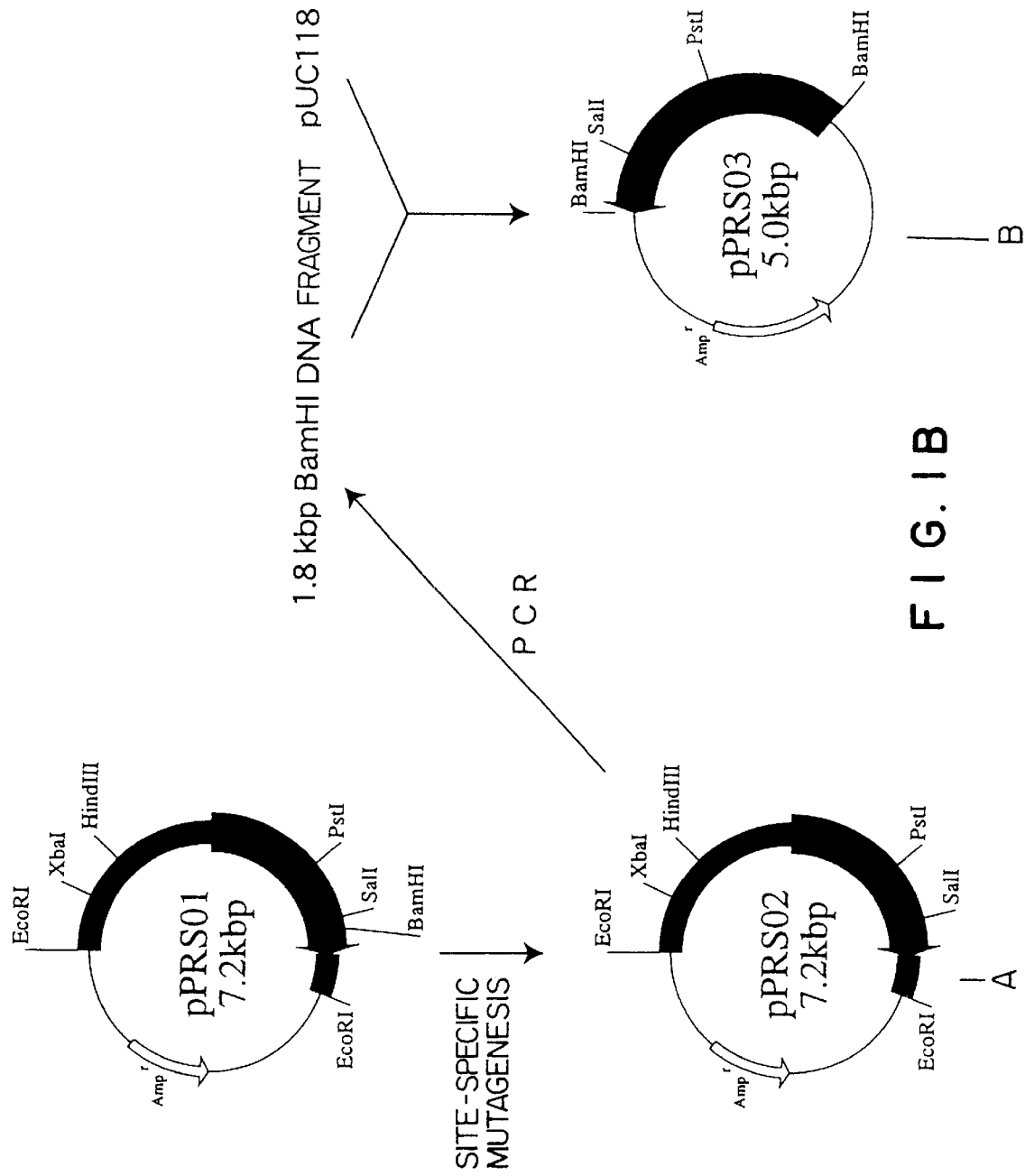
Figure 1C:
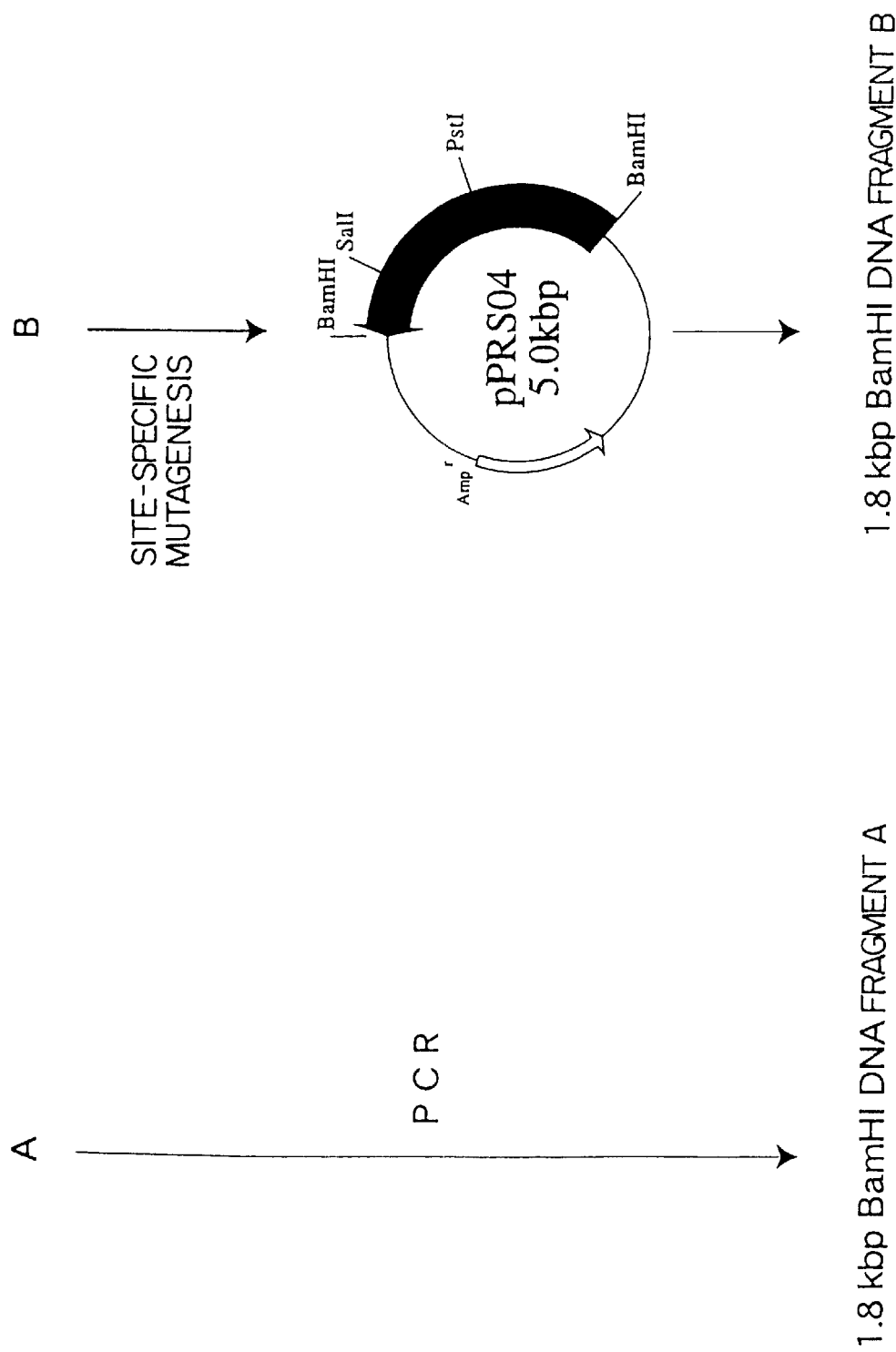
Figure 1D:
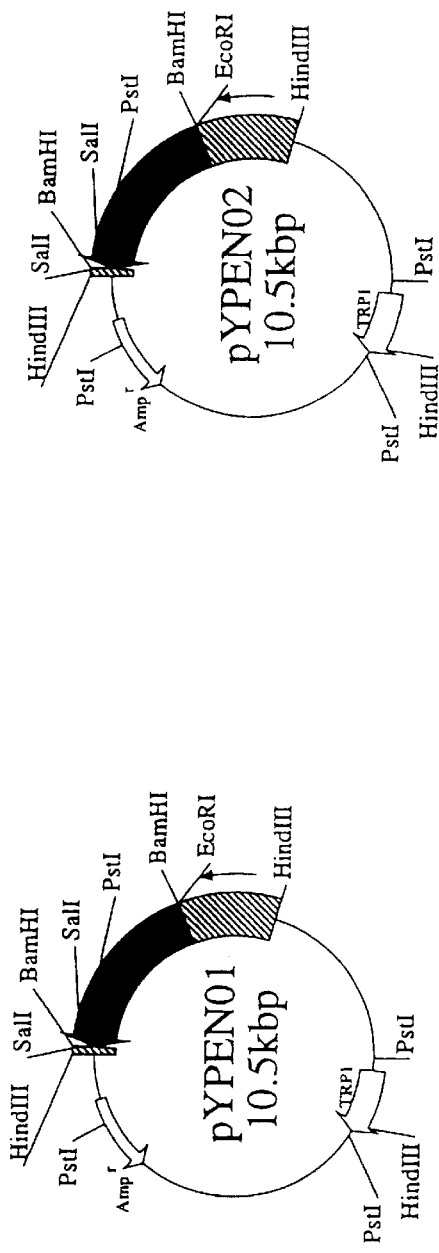

The polypeptide according to the present invention comprises the amino acid sequence of SEQ ID No. 1 or 3. This polypeptide having the amino acid sequence of SEQ ID No. 1 or 3 has enzymatic activity as β-fructofuranosidase. The polypeptide according to the present invention involves a homologue of the amino acid sequence of SEQ ID No. 1 or 3 as shown in the sequence listing. The term "homologue" refers to an amino acid sequence in which one or more amino acids (for example, one to several amino acids) are inserted, substituted or deleted in, or added to either or both of the terminals of, the amino acid sequence of SEQ ID Nos. 1 and 3 while retaining β-fructofuranosidase activity. Such a homologue can be selected and produced by those skilled in the art without undue experiments by referring to the sequence of SEQ ID No. 1 or 3.

The β-fructofuranosidase having the amino acid sequence of SEQ ID Nos. 1 and 3 according to the present invention has high fructosyltransferase activity and efficiently produces fructooligosaccharides. Specifically, when a sucrose solution at a concentration of 30 wt % or more is used as a substrate for reaction, the fructosyltransferase activity of β-fructofuranosidase having the amino acid sequence of SEQ ID No. 1 is at least 4 times higher, and the fructosyltransferase activity of β-fructofuranosidase having the amino acid sequence of SEQ ID No. 3 is at least 7 times higher than hydrolytic activity. Furthermore, 50% or more of sucrose is converted to fructooligosaccharides in both cases.

β-Fructofuranosidase gene

The novel gene encoding β-fructofuranosidase according to the present invention comprises a DNA sequence encoding the amino acid sequence of SEQ ID Nos. 1 and 3 or a homologue thereof.

Generally, a nucleotide sequence which encodes the amino acid sequence of a given protein can be easily determined from the reference chart known as "codon table". A variety of nucleotide sequence are available from those encoding the amino acid sequence of SEQ ID No. 1 or 3. Therefore, the term "a nucleotide sequence encoding the amino acid sequence of SEQ ID No. 1 or 3" refers to the meaning including the nucleotide sequence of SEQ ID No. 2 or 4, as well as nucleotide sequences which consist of the same codons as above allowing for degeneracy and encode the amino acid sequence of SEQ ID No. 1 or 3.

A preferred embodiment of the present invention provides, as a preferred example of the novel gene according to the present invention, a DNA fragment comprising the nucleotide sequence of SEQ ID No. 2 or 4.

As described above, the present invention encompasses a homologue of the amino acid sequence of SEQ ID No. 1 or 3. Therefore, the DNA fragment according to the present invention involves a nucleotide sequence which encodes such a homologue.

As the nucleotide sequence of the DNA fragment according to the present invention is determined, the DNA fragment may be obtained according to the procedure for the synthesis of a nucleic acid.

This sequence can also be obtained from *Penicillium roqueforti* or *Scopulariopsis brevicaulis*, preferably *Penicillium roqueforti* IAM7254 or *Scopulariopsis brevicaulis* IFO4843, according to the procedure of genetic engineering.

Expression of β-Fructofuranosidase Gene

The β-fructofuranosidase according to the present invention can be produced in a host cell which has been transformed by a DNA fragment encoding the enzyme. More specifically, a DNA fragment encoding the β-fructofuranosidase according to the present invention is introduced in a host cell in the form of a DNA molecule which is replicatable in the host cell and can express the above gene, particularly an expression vector, in order to transform the host cell. Then, the obtained transformant is cultivated.

Therefore, the present invention provides a DNA molecule which comprises a gene encoding the β-fructofuranosidase according to the present invention, particularly an expression vector. This DNA molecule is obtained by introducing a DNA fragment encoding the β-fructofuranosidase according to the present invention in a vector molecule. According to a preferred embodiment of the present invention, the vector is a plasmid.

The DNA molecule according to the present invention may be prepared by the standard technique of genetic engineering.

The vector applicable in the present invention can be selected as appropriate from viruses, plasmids, cosmid vectors, etc., considering the type of the host cell used. For example, a bacteriophage in the λ phage group or a plasmid in the pBR or pUC group may be used for *E coli* host cells, a plasmid in the pUB group for *Bacillus subtilis*, and a vector in the YEp or YCp group for yeast.

It is preferable that the plasmid contain a selectable marker to ensure the selection of the obtained transformance, such as a drug-resistance marker or marker gene complementing an auxotrophic mutation. Preferred example of marker genes include ampicillin-resistance gene, kanamycin-resistance gene, and tetracycline-resistance gene for bacterium host cells; N-(5'-phosphoribosyl)-anthranilate isomerase gene (TRP1), orotidine-5'-phosphate decarboxylase gene (URA3), and β-isopropylmalate dehydrogenase gene (LEU2) for yeast; and hygromycin-resistance gene (hph), bialophos-resistance gene (bar), and nitrate reductase gene (niaD) for mold.

It is also preferable that the DNA molecule for use as an expression vector according to the present invention contain nucleotide sequence necessary for the expression of the β-fructofuranosidase gene, including transcription and translation control signals, such as a promoter, a transcription initiation signal, a ribosome binding site, a translation termination signal, and a transcription termination signal.

Examples of preferred promoters include, in addition to the promoter on the inserted fragment which is able to function in the host, promoters such as those of lactose operon (lac), and tryptophan operon (trp) for *E. coli*; promoters such as those of alcohol dehydrogenase gene (ADH), acid phosphatase gene (PHO), galactose regulated gene (GAL), and glyceraldehyde-3-phosphate dehydrogenase gene (GPD) for yeast; and promoters such as those of a-amylase gene (amy) and cellobiohydrolase I gene (CBHI) for mold.

When the host cell is *Bacillus subtilis*, yeast or mold, it is also advantageous to use a secretion vector to allow it to extracellularly secrete the produced recombinant β-fructofuranosidase. Any host cell with an established host-vector system may be used, preferably yeast, mold, etc. It is preferable also to use the mold fungus having no β-fructofuranosidase activity described in PCT/JP97/00757.

A novel recombinant enzyme produced by the transformant described above is obtained by the following procedure: first, the host cell described above is cultivated under suitable conditions to obtain the supernatant or cell bodies from the resultant culture, using a known technique such as centrifugation; cell bodies should be further suspended in a suitable buffer solution, then homogenized by freeze-and-thaw, ultrasonic treatment, or mortar, followed by centrifugation or filtration to separate a cell body extract containing the novel recombinant enzyme.

The enzyme can be purified by combining the standard techniques for separation and purification. Examples of such as techniques include processes such as heat treatment, which rely on the difference in thermal resistance; processes such as salt sedimentation and solvent sedimentation, which rely on the difference in solubility; processes such as dialysis, ultrafiltration and gel filtration, and SDS-polyacrylamide gel electrophoresis, which rely on the difference in molecular weight; processes such as ion exchange chromatography, which rely on the difference in electric charge; processes such as affinity chromatography, which rely on specific affinity; processes such as hydrophobic chromatography and reversed-phase partition chromatography, which rely on the difference in hydrophobicity; and processes such as isoelectric focusing, which rely on the difference in isoelectric point.

Production of Fructooligosaccharides Using the β-Fructofuranosidase

The present invention further provides a process for producing fructooligosaccharide using the recombinant host or recombinant β-fructofuranosidase described above.

In the process for producing fructooligosaccharides according to the present invention, the recombinant host or recombinant β-fructofuranosidase described above is brought into contact with sucrose.

The mode and conditions where the recombinant host or recombinant β-fructofuranosidase according to the present invention comes in contact with sucrose are not limited in any way provided that the novel recombinant enzyme is able to act on sucrose. A preferred embodiment for contact in solution is as follows: The sucrose concentration may be selected as appropriate in the range where sucrose can be dissolved. However, considering the conditions such as the specific activity of the enzyme and reaction temperature, the concentration should generally fall in the range of 5% to 80%, preferably 30% to 70%. The temperature and pH for the reaction of sucrose by the enzyme should preferably be optimized for the characteristics of the novel recombinant enzyme. Therefore, the reasonable conditions are about 30° C. to 80° C., pH 4 to 10, preferably 40° C. to 70° C., pH 5 to 7.

The degree of purification of the novel recombinant enzyme may be selected as appropriate. The enzyme may be used either as unpurified in the form of supernatant from a transformant culture or cell body homogenate, as purified after processed in various purification steps, or as isolated after processed by various purification means.

Furthermore, the enzyme may be brought into contact with sucrose as fixed on a carrier using the standard technique.

The fructooligosaccharides thus produced are purified from the resulting solution according to known procedures. For example, the solution may be heated to inactivate the enzyme, decolorized using activated carbon, then desalted using ion exchange resin.

The present invention will now be described in more detail with reference to the following Examples. However, it is important to note that although the present invention has been described in considerable detail with reference to the following Examples, other examples are possible. Therefore, the spirit and scope of the appended claims should not be limited to the description of the Examples contained hereinbelow.

EXAMPLES

Example 1

Determination of Translation Region of β-Fructofuranosidase Gene from *Penicillium roqueforti* IAM7254

A DNA fragment of about 2 kbp containing the β-fructofuranosidase gene from *Aspergillus niger* was amplified by PCR using a chromosomal DNA prepared from *Aspergillus niger* ATCC20611 according to the standard procedure as a template and synthetic DNAs of SEQ ID Nos. 5 and 6 as primers. This DNA fragment was fractionated by agarose gel electrophoresis, extracted according to the standard procedure, purified, and then dissolved in sterilized water to 0.1 µg/µl to prepare a DNA sample for probe.

In the next step, a chromosomal DNA from *Penicillium roqueforti* IAM7254 was prepared, about 20 µg of the chromosomal DNA was digested completely with EcoRI, followed by agarose gel electrophoretsis to recover about 4 kbp DNA fragments.

The recovered DNA fragments of about 4 kbp (about 0.5 µg) were ligated with 1 µg of λgt10 vector which had been digested with EcoRI and treated with phosphatase, packaged using an in vitro packaging kit, GIGAPACK II Gold (Stratagene L.L.C.), and then introduced in *E. coli* NM514, to prepare a library.

A probe was prepared from DNA sample for probe above described. As a result of plaque hybridization using ECL Direct DNA/RNA Labelling & Detection System (Amersham International), 4 clones turned out positive in about 25,000 plaques. These positive clones were purified by a second screening to prepare phage DNA, which was then analyzed using restriction enzymes. The result showed that all the clones had an identical EcoRI fragment of about 4 kbp.

The EcoRI fragments of about 4 kbp were subdivided into a small fragment to select the desired DNA region using restriction enzymes, then subcloned to plasmid vector pUC118 or pUC119. The plasmid DNA was obtained from the subclone according to the standard procedure and sequenced using ALFred DNA Sequencer (Pharmacia) as shown in SEQ ID No. 7.

The sequence consisting 50 bases from 1695 to 1744 in this sequence was identified as an intron because it showed a typical intron structure of filamentous fungi. As a result, the sequence of SEQ ID No. 2 as a sequence encoding protein was obtained by deleting the intron from the sequence of SEQ ID No. 7. The encoded amino acid sequence was shown in SEQ ID No. 1.

Example 2

Expression of β-Fructofuranosidase Gene from *Penicillium roqueforti* IAM7254 in *Saccharomyces cerevisiae*

Plasmid pYPEN01 and pYPEN02 for expressing the β-fructofuranosidase gene from *Penicillium roqueforti* were prepared as follows (FIGS. 1A, B, C and D).

pYPR2831 (H. Horiuchi et al., Agric. Biol. Chem., 54, 1771–1779, 1990) was digested with EcoRI and SalI, and then its terminals were blunted with T4 DNA polymerase. The obtained fragment was ligated with BamHI linker (5'-CGGATCCG-3'), digested with BamHI, followed by self-ligation to obtain vector pY2831 for expression in yeast.

Next, single-stranded DNA was prepared from the plasmid pPRS01 obtained by inserting an about 4 kbp EcoRI DNA fragment containing the β-fructofuranosidase gene prepared in Example 1 into plasmid pUC118. Using the single-stranded DNA as a template and a synthetic DNA of SEQ ID No. 8 as a primer, the translated region of the β-fructofuranosidase gene was subjected to site-specific mutagenesis to disrupt the BamHI site without changing the encoded amino acid sequence (pPRS02).

A part of the translated region of the β-fructofuranosidase gene was prepared as an about 1.8 kbp BamHI fragment by PCR using plasmid pPRS02 as a template and synthetic DNAs of SEQ ID Nos. 9 and 10 as primers, and inserted into the BamHI site of plasmid pY2831 to prepare pYPEN01. Thus, plasmid pYPEN01 is designed to produce an enzyme protein comprising an amino acid sequence from 1 to 565 in the amino acid sequence of SEQ ID No. 1, which is a mature β-fructofuranosidase following secretion signal sequence.

Further, a DNA fragment containing the translated region of the β-fructofuranosidase gene was prepared as an about 1.8 kbp BamHI fragment by PCR using plasmid pPRS02 as a template and synthetic DNAs of SEQ ID Nos. 9 and 11 as primers, and inserted into the BamHI site of plasmid pUC118 to prepare plasmid pPRS03. A single-stranded DNA was prepared from plasmid pPRS03. As a result of site-specific mutagenesis using this as a template and a synthetic DNA of SEQ ID No. 12 as a primer, the intron sequence was removed (pPRS04). The translated region of the β-fructofuranosidase gene was prepared as an about 1.8 kbp BamHI fragment from plasmid pPRS04, and inserted into the BamHI site of plasmid pY2831 to prepare plasmid pYPEN02. Thus, plasmid pYPEN02 is designed to produce an enzyme protein comprising an amino acid sequence of SEQ ID No. 1, which is a mature β-fructofuranosidase following secretion signal sequence.

Plasmids pYPEN01 and pYPEN02 were introduced into *Saccharomyces cerevisiae* MS-161 (Suc⁻, ura3, trp1) by the lithium-acetate method (Ito, H. et al., J. Bacteriol., 153, 163–168, 1983) to obtain transformants. The transformants were cultivated in an SD-Ura medium (0.67% yeast nitrogen base (Difco), 2% glucose and 50 μg/ml uracil) at 30° C. overnight. The culture was seeded in a production medium (0.67% yeast nitrogen base (Difco), 2% glucosece, 2% casamino acid and 50 μg/ml uracil) at a final concentration of 1% and cultivated at 30° C. for 2 days. The culture supernatant was analyzed for β-fructofuranosidase activity, in units, i.e., the quantity of free glucose (μmol) released in 1 minute in 10 wt % sucrose solution, pH 5.5, at 40° C. for 60 minutes. As a result, the transformant with plasmid pYREN01 exhibited $4\times10^{-4}$ units/ml or less of activity while the transformant with plasmid pYREN02 exhibited 0.38 units/ml of activity.

Example 3

Determination of the Translated Region of β-Fructofuranosidase Gene from *Scopulariopsis brevicaulis* IFO4843

The chromosomal DNA was prepared from *Scopulariopsis brevicaulis* IFO4843. About 20 μg of a chromosomal DNA sample was completely digested with EcoRI, and electrophoresed through an agarose gel to recover an about 10 kbp DNA fragment.

The recovered DNA fragment of about 10 kbp (about 0.5 fig) were ligated with 1 μg of λDASHII vector digested with HindIII and EcorRI, and packaged using an in vitro packaging kit, GIGAPACK II Gold (Stratagene L.L.C.), then introduced in *E. coli* XL1-Blue MRA (P2), to prepare a library.

As a result of plaque hybridization using ECL Direct DNA/RNA Labelling & Detection System (Amersham International), with the about 2 kbp DNA fragment used in Example 1 as a probe, 3 clones turned out positive in about 15,000 plaques. These positive clones were purified by a second screening to prepare phage DNA, which was then analyzed using restriction enzymes. The result showed that all the clones had an identical EcorRI fragment of about 10 kbp.

These EcoRI fragments of about 10 kbp were subdivided into a small fragment to select the desired DNA region using restriction enzymes, then subcloned to plasmid vector pUC118 or pUC119. The plasmid DNA was obtained from the subclone according to the standard procedure and sequenced using ALFred DNA Sequencer (Pharmacia) as shown in SEQ ID No. 13.

The sequence comprising 55 bases from 1722 to 1776 in this sequence was identified as an intron because it showed a typical intron structure of filamentous fungi. As a result, the sequence of SEQ ID No. 4 as a sequence encoding protein was obtained by deleting the intron from the sequence of SEQ ID No. 13. The encoded amino acid sequence was shown SEQ ID No. 3.

Example 4

Expression of β-Fructofuranosidase Gene from *Scopulariopsis brevicaulis* IFO4843 in *Saccharomyces cerevisiae*

Figure 2A:
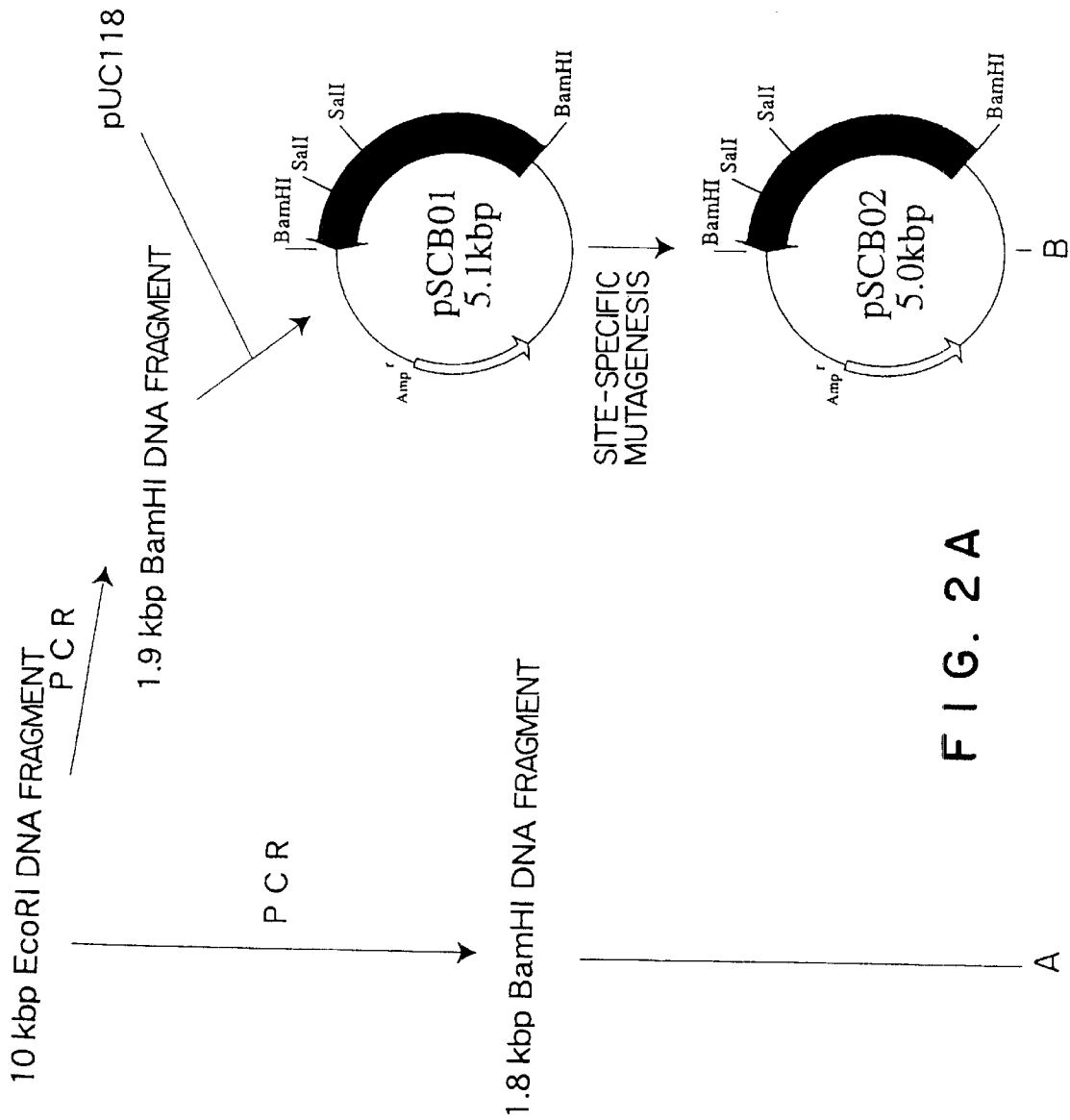
FIGS. 2A and B show the construction of expression vector pYSCOP02 in which a gene encoding the enzyme protein consisting of the amino acid sequence of SEQ ID No. 3 is introduced, and expression vector pYSCOP01 in which a gene encoding the enzyme protein consisting of the amino acid sequence from 1 to 574 of amino acid sequence of SEQ ID No. 3 is introduced.
Figure 2B:
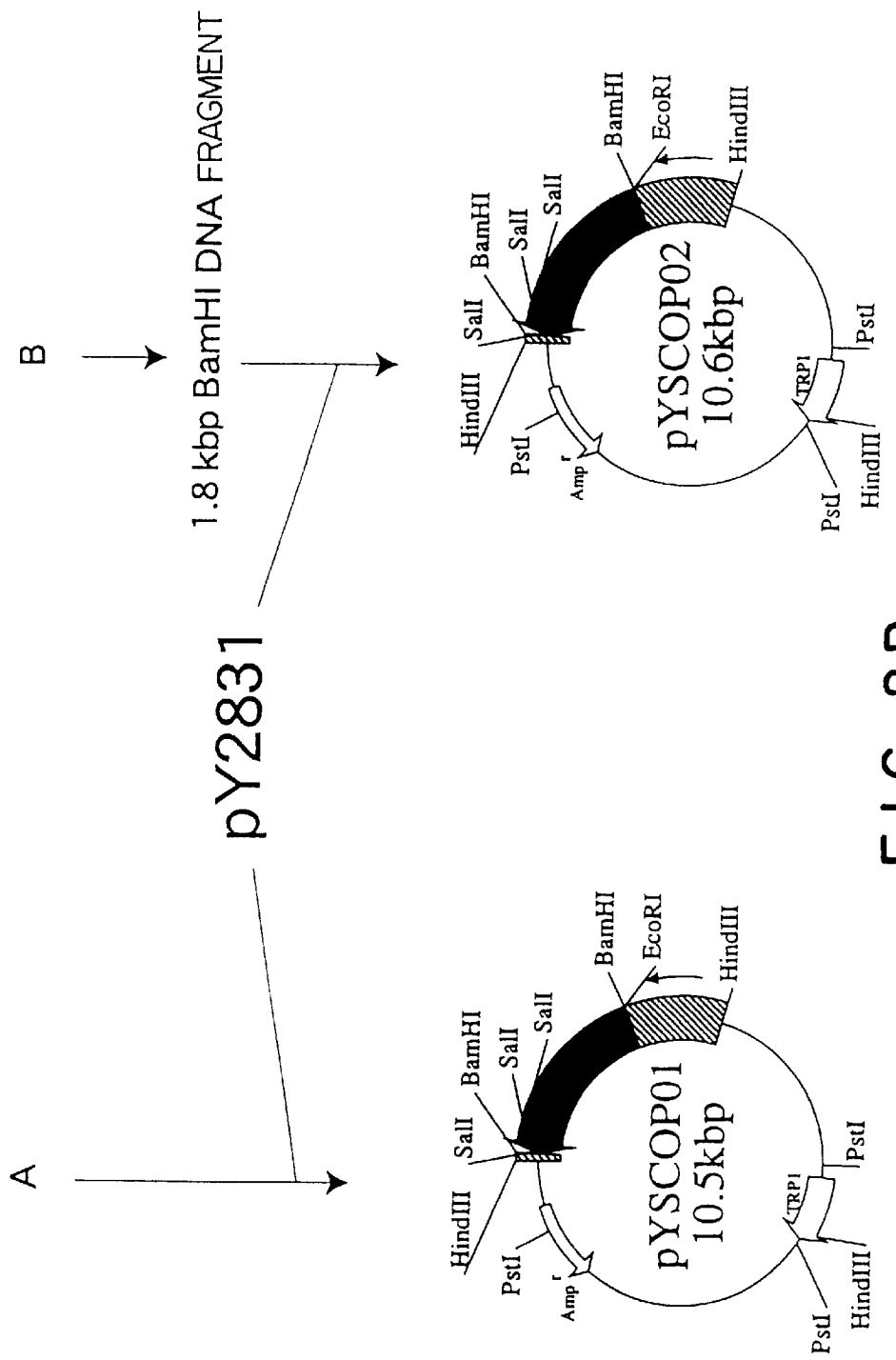

Plasmid pYSCOP01 and pYSCOP02 for expressing the β-fructofuranosidase gene from Scopulariopsis brevicaulis were prepared as follows (FIG. 2A and B).

A part of the translated region of the β-fructofuranosidase gene was prepared as an about 1.8 kbp BamHI fragment by PCR using about 10 kbp EcorRI DNA fragment prepared in Example 3 containing the β-fructofuranosidase gene as a template and synthetic DNAS of SEQ ID Nos. 14 and 15 as primers, and inserted into the BamHI site of plasmid pYSOP01 to prepare pYSCOP01. Thus, plasmid pYPEN01 is designed to produce an enzyme protein comprising an amino acid sequence from 1 to 574 in the amino acid sequence of SEQ ID No. 3, which is a mature β-fructofuranosidase following secretion signal sequence.

Next, a DNA fragment containing the translated region of the β-fructofuranosidase gene was prepared as an about 1.9 kbp BamHI fragment by PCR using an about 10 kbp EcorRI fragment containing the β-fructofuranosidase gene as a template and synthetic DNAs of SEQ ID Nos. 14 and 16 as primers, and inserted into the EcoRI site of plasmid pUC118 to prepare plasmid pSCB01. A single-stranded DNA was prepared from plasmid pSCB01. As a result of site-specific mutagenesis using this as a template and the synthetic DNA of SEQ ID No. 17 as a primer, the intron sequence was removed (pSCB02). The translated region of the β-fructofuranosidase gene was prepared as an about 1.9 kbp BamHI fragment from plasmid pSCB02, and inserted into the BamHI site of plasmid pY2831 to prepare plasmid pYSCOP02. Thus, plasmid pYSCOP02 is designed to produce an enzyme protein comprising an amino acid sequence of SEQ ID No. 3, which is a mature β-fructofuranosidase following secretion signal sequence.

Plasmids pYSCOP01 and pYSCOP02 were introduced into *Saccharomyces cerevisiae* MS-161 (Suc⁻, ura3, trp1) by the lithium-acetate method to obtain transformants. The transformants were cultivated in an SD-Ura medium at 30° C. overnight. The culture was seeded a production medium at a final concentration of 1% and cultivated at 30° C. for 2 days. The culture supernatant was analyzed for β-fructofuranosidase activity in the same manner as described in Example 2. As a result, the transformant with plasmid pYSCOP01 exhibited $4\times10^{-4}$ units/ml or less of activity, while the transformant with plasmid pYSCOP02 exhibited $6.5\times10^{-3}$ units/ml of activity.

---

What is claimed is:
1. An isolated polypeptide comprising the amino acid sequence of SEQ ID No. 1.

* * * * *

SEQUENCE LISTING

<160> NUMBER OF SEQ ID NOS: 17

<210> SEQ ID NO 1
<211> LENGTH: 603
<212> TYPE: PRT
<213> ORGANISM: Penicillium roqueforti IAM7254
<220> FEATURE:
<221> NAME/KEY: mat peptide
<222> LOCATION: (1)...(603)

<400> SEQUENCE: 1

```
Val Asp Phe His Thr Pro Ile Asp Tyr Asn Ser Ala Pro Pro Asn Leu
 1               5                  10                  15

Ser Thr Leu Ala Asn Ala Ser Leu Phe Lys Thr Trp Arg Pro Arg Ala
             20                  25                  30

His Leu Leu Pro Pro Ser Gly Asn Ile Gly Asp Pro Cys Gly His Tyr
         35                  40                  45

Thr Asp Pro Lys Thr Gly Leu Phe His Val Gly Trp Leu Tyr Ser Gly
     50                  55                  60

Ile Ser Gly Ala Thr Thr Asp Asp Leu Val Thr Tyr Lys Asp Leu Asn
65                  70                  75                  80

Pro Asp Gly Ala Pro Ser Ile Val Ala Gly Lys Asn Asp Pro Leu
                 85                  90                  95

Ser Val Phe Asp Gly Ser Val Ile Pro Ser Gly Ile Asp Gly Met Pro
                100                 105                 110

Thr Leu Leu Tyr Thr Ser Val Ser Tyr Leu Pro Ile His Trp Ser Ile
            115                 120                 125

Pro Tyr Thr Arg Gly Ser Glu Thr Gln Ser Leu Ala Val Ser Tyr Asp
        130                 135                 140

Gly Gly His Asn Phe Thr Lys Leu Asn Gln Gly Pro Val Ile Pro Thr
145                 150                 155                 160

Pro Pro Phe Ala Leu Asn Val Thr Ala Phe Arg Asp Pro Tyr Val Phe
                165                 170                 175

Gln Ser Pro Ile Leu Asp Lys Ser Val Asn Ser Thr Gln Gly Thr Trp
                180                 185                 190

Tyr Val Ala Ile Ser Gly Gly Val His Gly Val Gly Pro Cys Gln Phe
            195                 200                 205

Leu Tyr Arg Gln Asn Asp Ala Asp Phe Gln Tyr Trp Glu Tyr Leu Gly
        210                 215                 220

Gln Trp Trp Lys Glu Pro Leu Asn Thr Thr Trp Gly Lys Gly Asp Trp
225                 230                 235                 240

Ala Gly Gly Trp Gly Phe Asn Phe Glu Val Gly Asn Val Phe Ser Leu
                245                 250                 255

Asn Ala Glu Gly Tyr Ser Glu Asp Gly Glu Ile Phe Ile Thr Leu Gly
                260                 265                 270

Ala Glu Gly Ser Gly Leu Pro Ile Val Pro Gln Val Ser Ser Ile Arg
        275                 280                 285

Asp Met Leu Trp Val Thr Gly Asn Val Thr Asn Asp Gly Ser Val Thr
        290                 295                 300
```

-continued

```
Phe Lys Pro Thr Met Ala Gly Val Leu Asp Trp Gly Val Ser Ala Tyr
305                 310                 315                 320

Ala Ala Ala Gly Lys Ile Leu Pro Ala Ser Ser Gln Ala Ser Thr Lys
                325                 330                 335

Ser Gly Ala Pro Asp Arg Phe Ile Ser Tyr Val Trp Leu Thr Gly Asp
                340                 345                 350

Leu Phe Glu Gln Val Lys Gly Phe Pro Thr Ala Gln Gln Asn Trp Thr
                355                 360                 365

Gly Ala Leu Leu Leu Pro Arg Glu Leu Asn Val Arg Thr Ile Ser Asn
                370                 375                 380

Val Val Asp Asn Glu Leu Ser Arg Glu Ser Leu Thr Ser Trp Arg Val
385                 390                 395                 400

Ala Arg Glu Asp Ser Gly Gln Ile Asp Leu Glu Thr Met Gly Ile Ser
                405                 410                 415

Ile Ser Arg Glu Thr Tyr Ser Ala Leu Thr Ser Gly Ser Ser Phe Val
                420                 425                 430

Glu Ser Gly Lys Thr Leu Ser Asn Ala Gly Ala Val Pro Phe Asn Thr
                435                 440                 445

Ser Pro Ser Ser Lys Phe Phe Val Leu Thr Ala Asn Ile Ser Phe Pro
450                 455                 460

Thr Ser Ala Arg Asp Ser Gly Ile Gln Ala Gly Phe Gln Val Leu Ser
465                 470                 475                 480

Ser Ser Leu Glu Ser Thr Thr Ile Tyr Tyr Gln Phe Ser Asn Glu Ser
                485                 490                 495

Ile Ile Val Asp Arg Ser Asn Thr Ser Ala Ala Ala Arg Thr Thr Ala
                500                 505                 510

Gly Ile Leu Ser Asp Asn Glu Ala Gly Arg Leu Arg Leu Phe Asp Val
                515                 520                 525

Leu Arg Asn Gly Lys Glu Gln Val Glu Thr Leu Glu Leu Thr Ile Val
                530                 535                 540

Val Asp Asn Ser Val Leu Glu Val Tyr Ala Asn Gly Arg Phe Ala Leu
545                 550                 555                 560

Gly Thr Trp Ala Arg Ser Trp Tyr Ala Asn Ser Thr Lys Ile Asn Phe
                565                 570                 575

Phe His Asn Gly Val Gly Glu Ala Thr Phe Glu Asp Val Thr Val Phe
                580                 585                 590

Glu Gly Leu Tyr Asp Ala Trp Pro Gln Arg Lys
                595                 600

<210> SEQ ID NO 2
<211> LENGTH: 1809
<212> TYPE: DNA
<213> ORGANISM: Penicillium roqueforti IAM7254
<220> FEATURE:
<221> NAME/KEY: mat peptide
<222> LOCATION: (1)...(1809)

<400> SEQUENCE: 2
gttgatttcc ataccccgat tgactataac tcggctccgc caaacctttc taccctggca      60
aacgcatctc ttttcaagac atggagaccc agagcccatc ttctccctcc atctgggaac    120
ataggcgacc cgtgcgggca ctataccgat cccaagactg gtctcttcca cgtgggttgg    180
ctttacagtg ggatttcggg agcgacaacc gacgatctcg ttacctataa agacctcaat    240
cccgatggag ccccgtcaat tgttgcagga ggaaagaacg accctctttc tgtcttcgat    300
ggctcggtca ttccaagcgg tatagacggc atgccaactc ttctgtatac ctctgtatca    360
```

-continued

```
tacctcccaa tccactggtc catcccctac acccggggaa gcgagacaca atccttggcc    420
gtttcctatg acggtggtca caacttcacc aagctcaacc aagggcccgt gatccctacg    480
cctccgtttg ctctcaatgt caccgctttc cgtgacccct acgttttcca agcccaatt    540
ctggacaaat ctgtcaatag tacccaagga acatggtatg tcgccatatc tggcggtgtc    600
cacggtgtcg gaccttgtca gttcctctac cgtcagaaca cgcagattt tcaatattgg    660
gaatatctcg ggcaatggtg aaggagccc cttaatacca cttggggaaa gggtgactgg    720
gccgggggtt gggcttcaa ctttgaggtt ggcaacgtct ttagtctgaa tgcagagggg    780
tatagtgaag acggcgagat attcataacc ctcggtgctg agggttcggg acttcccatc    840
gttcctcaag tctcctctat tcgcgatatg ctgtgggtga ccggcaatgt cacaaatgac    900
ggctctgtca ctttcaagcc aaccatggcg ggtgtgcttg actggggcgt gtcggcatat    960
gctgctgcag gcaagatctt gccggccagc tctcaggcat ccacaaagag cggtgccccc   1020
gatcggttca tttcctatgt ctggctcact ggagatctat tcgagcaagt gaaaggattc   1080
cctaccgctc aacaaaactg gaccggggcc ctcttactgc cgcgagagct gaatgtccgc   1140
actatctcta acgtggtgga taacgaactt tcgcgtgagt ccttgacatc gtggcgcgtg   1200
gcccgcgaag actctggtca gatcgacctt gaaacaatgg gaatctcaat ttccagggag   1260
acttacagcg ctctcacatc cggctcatct tttgtcgagt ctggtaaaac gttgtcgaat   1320
gctggagcag tgcccttcaa tacctcaccc tcaagcaagt tcttcgtgct gacagcaaat   1380
atatctttcc cgacctctgc ccgtgactct ggcatccagg ctggtttcca ggttttatcc   1440
tctagtcttg agtctacaac tatctactac caattctcca acgagtccat catcgtcgac   1500
cgcagcaaca cgagtgctgc ggcgagaaca actgctggga tcctcagtga taacgaggcg   1560
ggacgtctgc gcctcttcga cgtgttgcga atggaaaag aacaggttga aactttggag   1620
ctcactatcg tggtggataa tagtgtactg gaagtatatg ccaatggacg ctttgctcta   1680
ggcacttggg ctcggtcttg gtacgccaac tcgactaaaa ttaacttctt ccataacggc   1740
gtgggagaag cgacattcga agatgtgacg gtctttgaag gactgtatga tgcctggcca   1800
caaaggaag                                                           1809
```

<210> SEQ ID NO 3
<211> LENGTH: 613
<212> TYPE: PRT
<213> ORGANISM: Scopulariopsis brevicaulis IFO4843
<220> FEATURE:
<221> NAME/KEY: mat peptide
<222> LOCATION: (1)...(613)

<400> SEQUENCE: 3

```
Gln Pro Thr Ser Leu Ser Ile Asp Asn Ser Thr Tyr Pro Ser Ile Asp
 1               5                  10                  15

Tyr Asn Ser Ala Pro Pro Asn Leu Ser Thr Leu Ala Asn Asn Ser Leu
                20                  25                  30

Phe Glu Thr Trp Arg Pro Arg Ala His Val Leu Pro Pro Gln Asn Gln
            35                  40                  45

Ile Gly Asp Pro Cys Met His Tyr Thr Asp Pro Glu Thr Gly Ile Phe
        50                  55                  60

His Val Gly Trp Leu Tyr Asn Gly Asn Gly Ala Ser Gly Ala Thr Thr
65                  70                  75                  80

Glu Asp Leu Val Thr Tyr Gln Asp Leu Asn Pro Asp Gly Ala Gln Met
                85                  90                  95
```

```
Ile Leu Pro Gly Gly Val Asn Asp Pro Ile Ala Val Phe Asp Gly Ala
            100                 105                 110
Val Ile Pro Ser Gly Ile Asp Gly Lys Pro Thr Met Met Tyr Thr Ser
        115                 120                 125
Val Ser Tyr Met Pro Ile Ser Trp Ser Ile Ala Tyr Thr Arg Gly Ser
    130                 135                 140
Glu Thr His Ser Leu Ala Val Ser Ser Asp Gly Gly Lys Asn Phe Thr
145                 150                 155                 160
Lys Leu Val Gln Gly Pro Val Ile Pro Ser Pro Phe Gly Ala Asn
                165                 170                 175
Val Thr Ser Trp Arg Asp Pro Phe Leu Phe Gln Asn Pro Gln Phe Asp
            180                 185                 190
Ser Leu Glu Ser Glu Asn Gly Thr Trp Tyr Thr Val Ile Ser Gly
        195                 200                 205
Gly Ile His Gly Asp Gly Pro Ser Ala Phe Leu Tyr Arg Gln His Asp
    210                 215                 220
Pro Asp Phe Gln Tyr Trp Glu Tyr Leu Gly Pro Trp Asn Glu Glu
225                 230                 235                 240
Gly Asn Ser Thr Trp Gly Ser Gly Asp Trp Ala Gly Arg Trp Gly Tyr
                245                 250                 255
Asn Phe Glu Val Ile Asn Ile Val Gly Leu Asp Asp Asp Gly Tyr Asn
            260                 265                 270
Pro Asp Gly Glu Ile Phe Ala Thr Val Gly Thr Glu Trp Ser Phe Asp
        275                 280                 285
Pro Ile Lys Pro Gln Ala Ser Asp Asn Arg Glu Met Leu Trp Ala Ala
    290                 295                 300
Gly Asn Met Thr Leu Glu Asp Gly Asp Ile Lys Phe Thr Pro Ser Met
305                 310                 315                 320
Ala Gly Tyr Leu Asp Trp Gly Leu Ser Ala Tyr Ala Ala Gly Lys
                325                 330                 335
Glu Leu Pro Ala Ser Ser Lys Pro Ser Gln Lys Ser Gly Ala Pro Asp
            340                 345                 350
Arg Phe Val Ser Tyr Leu Trp Leu Thr Gly Asp Tyr Phe Glu Gly His
        355                 360                 365
Asp Phe Pro Thr Pro Gln Gln Asn Trp Thr Gly Ser Leu Leu Pro
    370                 375                 380
Arg Glu Leu Ser Val Gly Thr Ile Pro Asn Val Val Asp Asn Glu Leu
385                 390                 395                 400
Ala Arg Glu Thr Gly Ser Trp Arg Val Gly Thr Asn Asp Thr Gly Val
                405                 410                 415
Leu Glu Leu Val Thr Leu Lys Gln Glu Ile Ala Arg Glu Thr Leu Ala
            420                 425                 430
Glu Met Thr Ser Gly Asn Ser Phe Thr Glu Ala Ser Arg Asn Val Ser
        435                 440                 445
Ser Pro Gly Ser Thr Ala Phe Gln Gln Ser Leu Asp Ser Lys Phe Phe
    450                 455                 460
Val Leu Thr Ala Ser Leu Ser Phe Pro Ser Ser Ala Arg Asp Ser Asp
465                 470                 475                 480
Leu Lys Ala Gly Phe Glu Ile Leu Ser Ser Glu Phe Glu Ser Thr Thr
                485                 490                 495
Val Tyr Tyr Gln Phe Ser Asn Glu Ser Ile Ile Asp Arg Ser Asn
            500                 505                 510
```

```
Ser Ser Ala Ala Ala Leu Thr Thr Asp Gly Ile Asp Thr Arg Asn Glu
        515                 520                 525

Phe Gly Lys Met Arg Leu Phe Asp Val Val Glu Gly Asp Gln Glu Arg
        530                 535                 540

Ile Glu Thr Leu Asp Leu Thr Ile Val Val Asp Asn Ser Ile Val Glu
545                 550                 555                 560

Val His Ala Asn Gly Arg Phe Ala Leu Ser Thr Trp Val Arg Ser Trp
                565                 570                 575

Tyr Glu Ser Ser Lys Asp Ile Lys Phe Phe His Asp Gly Asp Ser Thr
                580                 585                 590

Val Gln Phe Ser Asn Ile Thr Val Tyr Glu Gly Leu Phe Asp Ala Trp
        595                 600                 605

Pro Glu Arg Ala Arg
        610

<210> SEQ ID NO 4
<211> LENGTH: 1839
<212> TYPE: DNA
<213> ORGANISM: Scopulariopsis brevicaulis IFO4843
<220> FEATURE:
<221> NAME/KEY: mat peptide
<222> LOCATION: (1)...(1839)

<400> SEQUENCE: 4
caacctacgt ctctgtcaat cgacaattcc acgtatcctt ctatcgacta caactccgcc      60
cctccaaacc tctcgactct tgccaacaac agcctcttcg agacatggag gccgagggca     120
cacgtccttc cgccccagaa ccagatcggc gatccgtgta tgcactacac cgaccccgag     180
acaggaatct tccacgtcgg ctggctgtac aacggcaatg cgcttccgg cgccacgacc      240
gaggatctcg tcacctatca ggatctcaac ccgacggag cgcagatgat ccttccgggt      300
ggtgtgaatg accccattgc tgtctttgac ggcgcggtta ttcccagtgg cattgatggg      360
aaacccacca tgatgtatac ctcggtgtca tacatgccca tctcctggag catcgcttac     420
accaggggaa gcgagaccca ctctctcgca gtgtcgtccg acggcggtaa gaacttcacc     480
aagctggtgc agggccccgt cattccttcg cctcccttcg gcgccaacgt gaccagctgg     540
cgtgaccct tcctgttcca aaaccccag ttcgactctc tcctcgaaag cgagaacggc       600
acgtggtaca ccgttatctc tggtggcatc cacggtgacg ccccctccgc gttcctctac     660
cgtcagcacg accccgactt ccagtactgg gagtaccttg accgtggtg gaacgaggaa      720
gggaactcga cctggggcag cggtgactgg gctgccggt ggggctacaa cttcgaggtc      780
atcaacattg tcggtcttga cgatgatggc tacaaccccg acggtgaaat ctttgccacg     840
gtaggtaccg aatggtcgtt tgaccccatc aaaccgcagg cctcggacaa cagggagatg     900
ctctgggccg cggcaacat gactctcgag gacggcgata tcaagttcac gccaagcatg     960
gcgggctacc tcgactgggg tctatcggcg tatgccgccg ctggcaagga gctgcccgct    1020
tcttcaaagc cttcgcagaa gagcggtgcg ccggaccggt tcgtgtcgta cctgtggctc    1080
accggtgact acttcgaggg ccacgacttc cccaccccgc agcagaattg gaccggctcg    1140
cttttgcttc cgcgtgagct gagcgtcggg acgattccca acgttgtcga caacgagctt    1200
gctcgcgaga cgggctcttg gagggttggc accaacgaca ctggcgtgct tgagctggtc    1260
actctgaagc aggagattgc tcgcgagacg ctggctgaaa tgaccagcgg caactccttc    1320
accgaggcga gcaggaatgt cagctcgccc ggatctaccg ccttccagca gtccctggat    1380
tccaagttct tcgtcctgac cgcctcgctc tccttcccctt cgtcggctcg cgactccgac    1440
```

```
ctcaaggctg gtttcgagat cctgtcgtcc gagtttgagt cgaccacggt ctactaccag    1500
ttttccaacg agtccatcat cattgaccgg agcaactcga gtgctgccgc cttgactacc    1560
gatggaatcg acacccgcaa cgagtttggc aagatgcgcc tgtttgatgt tgtcgagggt    1620
gaccaggagc gtatcgagac gctcgatctc actattgtgg ttgataactc gatcgttgag    1680
gttcatgcca acggcgatt cgctctgagc acttgggttc gttcgtggta cgagtcgtcc    1740
aaggacatca agttcttcca cgatggcgac agcacggttc agttctcgaa catcaccgtc    1800
tacgagggac tgtttgacgc ctggccggag cgggccagg                          1839
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: DNA PRIMER

<400> SEQUENCE: 5

```
caatgaagct caccactacc                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: DNA PRIMER

<400> SEQUENCE: 6

```
atcccggtca atttctctcc                                                 20
```

<210> SEQ ID NO 7
<211> LENGTH: 1859
<212> TYPE: DNA
<213> ORGANISM: Penicillium roqueforti IAM7254
<220> FEATURE:
<221> NAME/KEY: CDS
<222> LOCATION: (1)...(1694)
<221> NAME/KEY: intron
<222> LOCATION: (1695)...(1744)
<221> NAME/KEY: CDS
<222> LOCATION: (1745)...(1859)

<400> SEQUENCE: 7

```
gttgatttcc ataccccgat tgactataac tcggctccgc caaacctttc taccctggca     60
aacgcatctc ttttcaagac atggagaccc agagcccatc ttctccctcc atctgggaac    120
ataggcgacc cgtgcgggca ctataccgat cccaagactg gtctcttcca cgtgggttgg    180
ctttacagtg ggatttcggg agcgacaacc gacgatctcg ttacctataa agacctcaat    240
cccgatggag ccccgtcaat tgttgcagga ggaaagaacg accctctttc tgtcttcgat    300
ggctcggtca ttccaagcgg tatagacggc atgccaactc ttctgtatac ctctgtatca    360
tacctcccaa tccactggtc catccctac acccggggaa gcgagacaca atccttggcc    420 gttcctatg acggtggtca aacttcacc aagctcaacc aagggcccgt gatccctacg     480
cctccgtttg ctctcaatgt caccgctttc cgtgacccct acgttttcca agcccaatt    540 ctggacaaat ctgtcaatag tacccaagga acatggtatg tcgccatatc tggcggtgtc    600
cacggtgtcg gaccttgtca gttcctctac cgtcagaacg acgcagattt tcaatattgg    660
gaatatctcg ggcaatggtg gaaggagccc cttaatacca cttggggaaa gggtgactgg    720 gccggggggtt ggggcttcaa ctttgaggtt ggcaacgtct ttagtctgaa tgcagagggg    780
```

```
tatagtgaag acggcgagat attcataacc ctcggtgctg agggttcggg acttcccatc    840
gttcctcaag tctcctctat tcgcgatatg ctgtgggtga ccggcaatgt cacaaatgac    900
ggctctgtca ctttcaagcc aaccatggcg ggtgtgcttg actggggcgt gtcggcatat    960
gctgctgcag gcaagatctt gccggccagc tctcaggcat ccacaaagag cggtgccccc   1020
gatcggttca tttcctatgt ctggctcact ggagatctat tcgagcaagt gaaaggattc   1080
cctaccgctc aacaaaactg gaccggggcc ctcttactgc cgcgagagct gaatgtccgc   1140
actatctcta acgtggtgga taacgaactt tcgcgtgagt ccttgacatc gtggcgcgtg   1200
gcccgcgaag actctggtca gatcgacctt gaaacaatgg gaatctcaat ttccagggag   1260
acttacagcg ctctcacatc cggctcatct tttgtcgagt ctggtaaaac gttgtcgaat   1320
gctggagcag tgcccttcaa tacctcaccc tcaagcaagt tcttcgtgct gacagcaaat   1380
atatctttcc cgacctctgc ccgtgactct ggcatccagg ctggtttcca ggttttatcc   1440
tctagtcttg agtctacaac tatctactac caattctcca acgagtccat catcgtcgac   1500
cgcagcaaca cgagtgctgc ggcgagaaca actgctggga tcctcagtga taacgaggcg   1560
ggacgtctgc gcctcttcga cgtgttgcga aatggaaaag aacaggttga aactttggag   1620
ctcactatcg tggtggataa tagtgtactg gaagtatatg ccaatggacg ctttgctcta   1680
ggcacttggg ctcggtaagt ctctcttgtt tatggaagat tggtcaaaaa ctaaccgcat   1740
gaaggtcttg gtacgccaac tcgactaaaa ttaacttctt ccataacggc gtgggagaag   1800
cgacattcga agatgtgacg gtctttgaag gactgtatga tgcctggcca caaggaag     1859
```

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: DNA PRIMER

<400> SEQUENCE: 8
caactgctgg catcctcagt ga                                               22

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: DNA PRIMER

<400> SEQUENCE: 9
gcggatccat gaagctatca aatgcaatc                                        29

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: DNA PRIMER

<400> SEQUENCE: 10
gcggatcctt accgagccca agtgcc                                           26

<210> SEQ ID NO 11
<211> LENGTH: 27
<212> TYPE: DNA
<213> ORGANISM: Artificial Sequence
<220> FEATURE:

```
<223> OTHER INFORMATION: Description of Artificial Sequence: DNA PRIMER

<400> SEQUENCE: 11
gcggatcctc acttcctttg tggccag                                          27

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: DNA PRIMER

<400> SEQUENCE: 12
gttggcgtac caagaccgag cccaagtgcc                                       30

<210> SEQ ID NO 13
<211> LENGTH: 1894
<212> TYPE: DNA
<213> ORGANISM: Scopulariopsis brevicaulis IFO4843
<220> FEATURE:
<221> NAME/KEY: CDS
<222> LOCATION: (1)...(1721)
<221> NAME/KEY: intron
<222> LOCATION: (1722)...(1776)
<221> NAME/KEY: CDS
<222> LOCATION: (1777)...(1894)

<400> SEQUENCE: 13
caacctacgt ctctgtcaat cgacaattcc acgtatcctt ctatcgacta caactccgcc      60
cctccaaacc tctcgactct tgccaacaac agcctcttcg agacatggag gccgagggca     120
cacgtccttc cgccccagaa ccagatcggc gatccgtgta tgcactacac cgaccccgag     180
acaggaatct tccacgtcgg ctggctgtac aacggcaatg gcgcttccgg cgccacgacc     240
gaggatctcg tcacctatca ggatctcaac cccgacggag cgcagatgat ccttccgggt     300
ggtgtgaatg accccattgc tgtctttgac ggcgcggtta ttcccagtgg cattgatggg     360
aaacccacca tgatgtatac ctcggtgtca tacatgccca tctcctggag catcgcttac     420
accaggggaa gcgagaccca ctctctcgca gtgtcgtccg acggcggtaa gaacttcacc     480
aagctggtgc agggccccgt cattccttcg cctcccttcg cgccaacgt gaccagctgg     540 cgtgacccct tcctgttcca aaaccccag ttcgactctc tcctcgaaag cgagaacggc     600
acgtggtaca ccgttatctc tggtggcatc cacggtgacg gcccctccgc gttcctctac     660
cgtcagcacg acccccgactt ccagtactgg gagtaccttg accgtggtg gaacgaggaa     720 gggaactcga cctggggcag cggtgactgg gctggccggt ggggctacaa cttcgaggtc     780
atcaacattg tcggtcttga cgatgatggc tacaaccccg acgtgaaat cttttgccacg     840 gtaggtaccg aatggtcgtt tgaccccatc aaaccgcagg cctcggacaa cagggagatg     900
ctctgggccg cgggcaacat gactctcgag gacggcgata tcaagttcac gccaagcatg     960
gcgggctacc tcgactgggg tctatcggcg tatgccgccg ctggcaagga gctgcccgct    1020
tcttcaaagc cttcgcagaa gagcggtgcg ccggaccggt tcgtgtcgta cctgtggctc    1080
accggtgact acttcgaggg ccacgacttc cccacccgc agcagaattg gaccggctcg    1140
cttttgcttc cgcgtgagct gagcgtcggg acgattccca acgttgtcga caacgagctt    1200
gctcgcgaga cgggctcttg gagggttggc accaacgaca ctggcgtgct tgagctggtc    1260
actctgaagc aggagattgc tcgcgagacg ctggctgaaa tgaccagcgg caactccttc    1320
accgaggcga gcaggaatgt cagctcgccc ggatctaccg ccttccagca gtccctggat    1380
```

-continued

```
tccaagttct tcgtcctgac cgcctcgctc tccttcccct cgtcggctcg cgactccgac      1440
ctcaaggctg gtttcgagat cctgtcgtcc gagtttgagt cgaccacggt ctactaccag      1500
ttttccaacg agtccatcat cattgaccgg agcaactcga gtgctgccgc cttgactacc      1560
gatggaatcg acacccgcaa cgagtttggc aagatgcgcc tgtttgatgt tgtcgagggt      1620
gaccaggagc gtatcgagac gctcgatctc actattgtgg ttgataactc gatcgttgag      1680
gttcatgcca acgggcgatt cgctctgagc acttgggttc ggtaagtgga acgccgacca      1740
cgcttcttaa tttctccaat actaacatta tcacagttcg tggtacgagt cgtccaagga      1800
catcaagttc ttccacgatg gcgacagcac ggttcagttc tcgaacatca ccgtctacga      1860
gggactgttt gacgcctggc cggagcgggc cagg                                  1894
```

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: DNA PRIMER

<400> SEQUENCE: 14
gcggatccat gaaactctca actgtt                                              26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: DNA PRIMER

<400> SEQUENCE: 15
gcggatcctt accgaaccca agtgct                                              26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: DNA PRIMER

<400> SEQUENCE: 16
gcggatcctt acctggcccg ctccg                                               25

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: DNA PRIMER

<400> SEQUENCE: 17
cgactcgtac cacgaacgaa cccaagtgct cag 33